United States Patent [19]
Pesnicak

[11] Patent Number: 5,810,773
[45] Date of Patent: Sep. 22, 1998

[54] MIXING ARRANGEMENT AND METHOD

[75] Inventor: Lesley Pesnicak, Stafford, Va.

[73] Assignee: The United States of America as represented by the Department of Health and Human Services, Washington, D.C.

[21] Appl. No.: 823,417

[22] Filed: Mar. 25, 1997

[51] Int. Cl.$^6$ .................................................. A61M 37/00
[52] U.S. Cl. .............................................. 604/83; 604/82
[58] Field of Search .................................. 604/82, 83, 85, 604/86, 187

[56] References Cited

U.S. PATENT DOCUMENTS 5,190,524  3/1993  Wex ........................................ 604/83 X
5,190,525  3/1993  Oswald et al. ............................ 604/83

Primary Examiner—Wynn Wood Coggins
Assistant Examiner—N. Kent Gring
Attorney, Agent, or Firm—Merchant, Gould, Smith, Edell, Welter & Schmidt, P.A.

[57] ABSTRACT

An arrangement for mixing together two fluids includes a base and first, second, and third holding members each secured to the base. The first holding member is constructed and arranged to hold a first fluid holding device, such as a syringe, relative to a second fluid holding device, such as a syringe, and a connector. The second holding member is constructed and arranged to hold the second fluid holding device relative to the first fluid holding device and the connector. The third holding member is constructed and arranged to hold the connector relative to the first fluid holding device and second fluid holding device. The third holding member is positioned on the base in axial alignment with both the first holding member and the second holding member. A method for mixing two fluids includes connecting first and second syringes with a three-way stopcock. The connected syringes are positioned on a base containing three holding members. The fluids are pumped back and forth between the two syringes in order to mix the fluids.

18 Claims, 2 Drawing Sheets

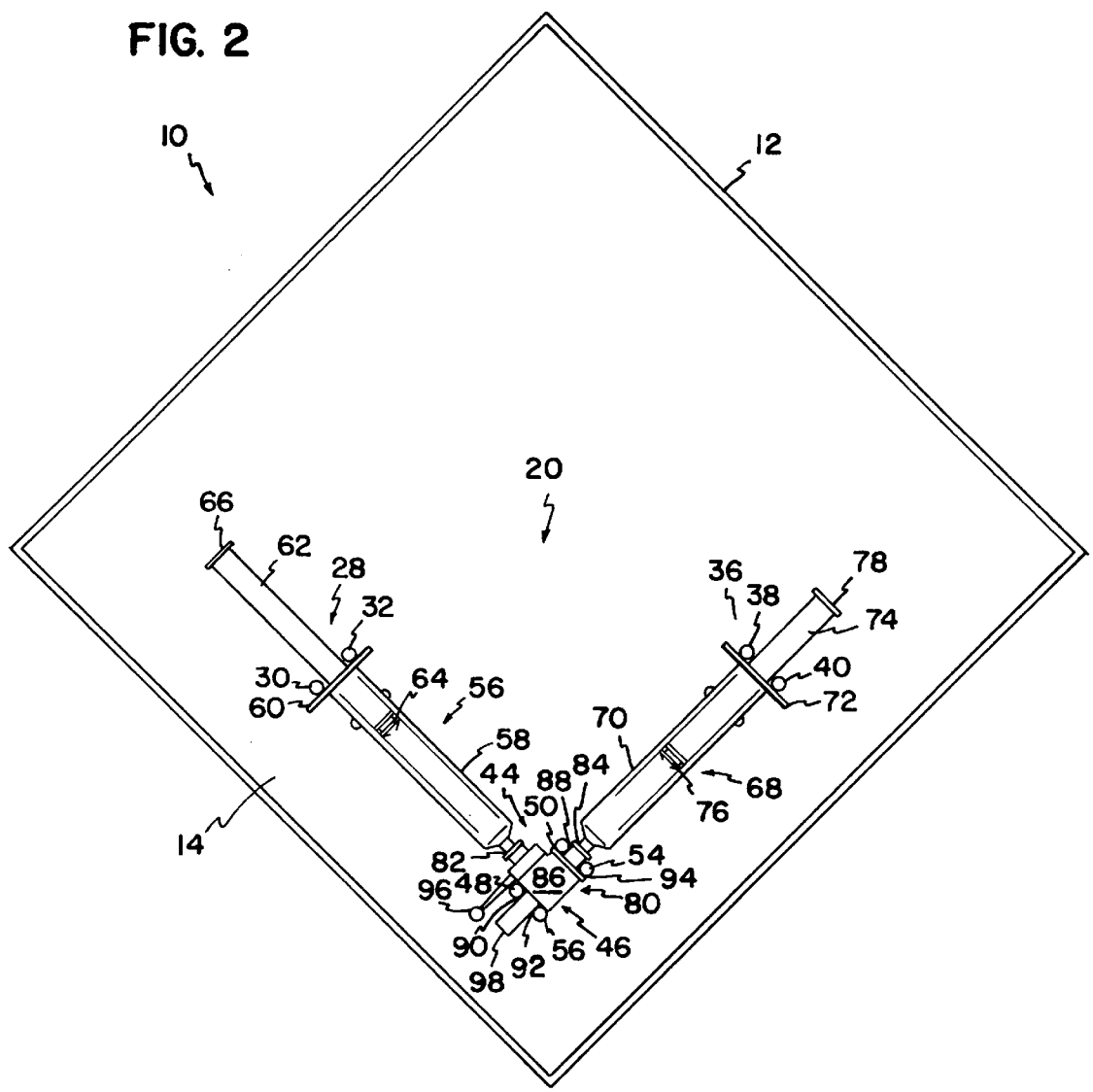

MIXING ARRANGEMENT AND METHOD

FIELD OF THE INVENTION

This invention relates generally to an arrangement and method for mixing together two fluids. More particularly, this invention relates to an arrangement and method for emulsifying adjuvant with antigens.

BACKGROUND OF THE INVENTION

In laboratory experiments, it is sometimes desirable to mix together two fluids. One way of accomplishing this is by linearly connecting two syringes, each containing one of the fluids, with a connector. The fluids are pumped back and forth between the two syringes and connector to mix the two fluids. Upon completion of the mixing, all of the mixture is drawn into just one of the syringes.

One use of this process is for creating an emulsification of adjuvant and antigens. The adjuvant is introduced into one syringe, and the antigens are introduced into another syringe. These syringes are connected together with a connector. To mix the adjuvant with the antigens, one of the syringe's plungers is depressed to push the fluid through the connector to the other syringe. Then, the other syringe's plunger is depressed to push the fluid back to the first syringe. This back-and-forth is continued until the fluids are sufficiently mixed and drawn up into a single syringe. When emulsifying adjuvant and antigens, the desired consistency of the emulsion is a thick paste. This can lead to problems. For example, the thick consistency of the emulsion often causes the syringes to "blow apart" at the connector being used between the syringes. A connector blow-out is especially likely when small amounts of emulsions are needed for small animals. This can be a costly loss of material and time, and may also contribute to frustration of the laboratory technicians. Further, the connector can be difficult to clean due to its shape, and especially if the mixture is a thick paste, which tends to stick to the sides.

SUMMARY OF THE INVENTION

The present invention is directed to an arrangement for mixing together two fluids. To achieve the advantages of the invention and in accordance with the purposes of the invention, as embodied and broadly described herein, the invention comprises an arrangement for mixing together two fluids. The arrangement includes a base including a supporting surface, and first, second, and third holding members each secured to the base. The first holding member is constructed and arranged to hold a first syringe relative to a second syringe and a connector. The second holding member is constructed and arranged to hold the second syringe relative to the first syringe and connector. The second holding member is positioned on the base to hold the second syringe at a first angle from the first syringe. The third holding member is constructed and arranged to hold the connector relative to the first syringe and second syringe. The third holding member is positioned on the base in axial alignment with both the first holding member and the second holding member.

Preferably, the first holding member includes a first pair of stops extending from the base. Preferably, the second holding member includes a second pair of stops extending from the base. It is also preferred that the third holding member includes a third and a fourth pair of stops extending from the base.

The first angle may be about 90°. The base may comprise plexiglass being substantially rectangular.

Preferably, a first syringe is held by the first holding member, wherein the first syringe includes a first barrel for containing a first fluid, and a first plunger slidably positioned within the first barrel. The first barrel includes a first flange surface engaging the first pair of stops.

Preferably, a second barrel is held by the second holding member, wherein the second syringe includes a second barrel for containing a second fluid, and a second plunger slidably positioned within the second barrel. The second barrel includes a second flange surface engaging the second pair of stops.

Preferably, a connector connects the first and second syringes, wherein the connector is held by and positioned between the third and fourth pairs of stops. The connector may include a 3-way stopcock.

The first pair of stops may define a first gap therebetween, where the first plunger is slidably positioned within the first gap. Similarly, the second pair of stops may define a second gap therebetween, where the second plunger is slidably positioned within the second gap.

In certain arrangements, each of the first, second, third, and fourth pairs of stops comprises removable pegs.

In another aspect, the invention comprises a mixing apparatus including a base having a mounting surface, a first syringe positioned on the mounting surface, a second syringe positioned on the mounting surface, a connector connecting the first syringe and the second syringe, and a locking arrangement secured to the base. The locking arrangement is constructed and arranged to prevent the connector from disengaging from both the first and second syringes.

Preferably, the locking arrangement includes a first stop member engaging the first syringe, a second stop member engaging the second syringe, and a third stop member engaging the connector.

Preferably, the first stop member includes a first pair of pegs, and the first syringe includes a first flange and a first plunger. The first flange engages the first pair of pegs, and the plunger is slidably positioned between each of the first pair of pegs. The second stop member includes a second pair of pegs, and a second syringe includes a second flange and a second plunger. The second flange engages the second pair of pegs, and the second plunger is slidably positioned between each of the second pair of pegs. The connector comprises a three-way stopcock having at least four exterior corners. The third stop member includes at least four pegs, wherein each of the four pegs engages the stopcock at a respective one of the exterior corners.

Preferably, the first syringe is positioned about 90° with respect to the second syringe. The base may comprise plexiglass.

In another aspect, the invention comprises a method for mixing. The method includes providing a base including first, second, and third holding members all secured to the base. A first syringe holding a first fluid is connected to a second syringe holding a second fluid by using a three-way stopcock. Next, the connected syringes are positioned on the base by engaging a first surface of the first syringe with the first holding member, engaging a second surface of the second syringe with the second holding member, and engaging the stopcock with the third holding member.

Preferably, after the step of positioning, the method includes a step of mixing the first and second fluids by pumping the first and second fluids back and forth between the first and second syringes.

Preferably, the positioning step includes engaging a flange of the first syringe against a stop on the base, engaging a flange on the second syringe with a stop on the base, and engaging exterior corner surfaces on the stopcock with stops on the base.

Preferably, the mixing step includes mixing adjuvant with antigens.

It is to be understood that both the foregoing general description and the following detailed description are exemplary and explanatory only and are not restrictive of the invention, as claimed.

The accompanying drawings, which are incorporated in and constitute a part of this specification, illustrate one embodiment of the invention and together with the description, serve to explain the principles of the invention. In the drawings:

BRIEF DESCRIPTION OF THE DRAWINGS

FIG. 2 is a top plan view of the mixing arrangement depicted in FIG. 1 with additional mixing components, according to the present invention.

DETAILED DESCRIPTION OF PREFERRED EMBODIMENTS

Figure 1:
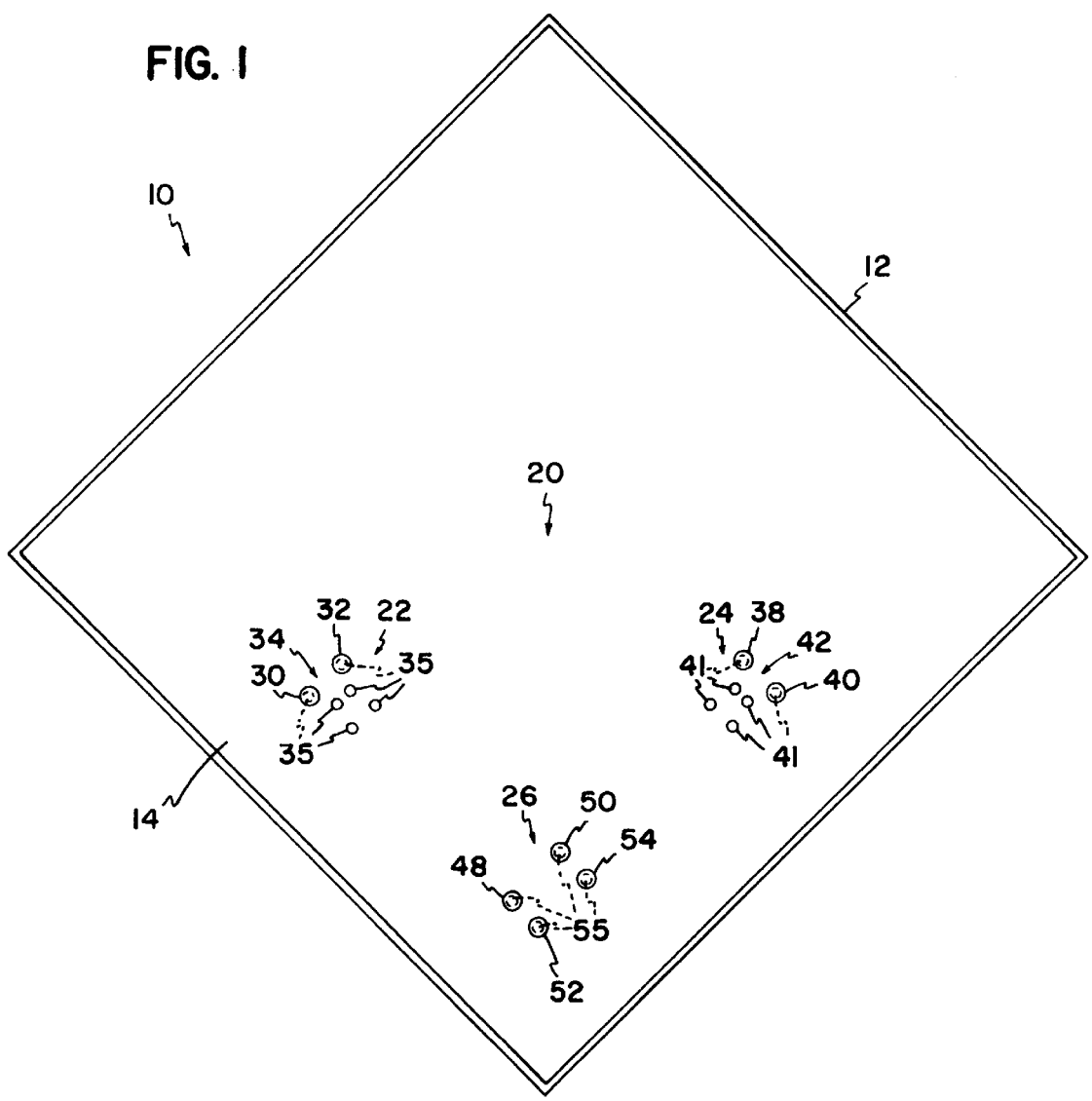
FIG. 1 is a top plan view of an embodiment of a mixing arrangement, according to the present invention.

Reference will now be made in detail to the present preferred embodiments of the invention, an example which is illustrated in the accompanying drawings.

The mixing arrangement of the present invention solves the problem of connector blow-out. The invention includes a base with a plurality of holders, or lock members, for locking the syringes relative to each other. The holders permit two fluids to be mixed together, and prevent the syringes from disengaging. The various components may be disposable, so there is no possibility for contamination. The arrangement avoids having to use special luer-locks. As such, it helps to reduce fatigue in lab personnel who may tire from having to do extensive manipulations, such as with arrangements in the prior art.

In accordance with the invention, the invention comprises an arrangement for mixing together two fluids. As embodied herein, a mixing arrangement is shown generally in FIGS. 1 and 2 at 10. Arrangement 10 is usable to mix together any two fluids. However, it has been found to be particularly advantageous in the preparation of emulsification of peptide antigens with adjuvants. Mixing arrangement 10 includes a base 12 for supporting the structure used to mix together two fluids. Base 12 includes a substantially planar, supporting or mounting surface 14 and an oppositely disposed resting surface for engaging the lab countertop, or whatever surface base 12 rests upon. Base 12 may be a variety of shapes, so long as it allows for the fluids to be mixed together and avoids blow-out. In the specific embodiment illustrated in FIGS. 1 and 2, base 12 is rectangular, in plan view. Base 12 may be comprised of a variety of materials, so long as it is sufficiently rigid to securely hold the structure for mixing. Preferred materials for base 12 include plexiglass. Other suitable materials include wood, fiber board, or plastic.

In accordance with the invention, the mixing arrangement includes a locking arrangement constructed and arranged to secure fluid holding devices in order to prevent a connector which connects the fluid holding devices together from disengaging. As embodied herein, a locking arrangement is shown generally at 20 secured to mounting surface 14 of base 12. Locking arrangement 20 holds the fluid holding devices and connector securely in place so that a blow-out at the connector is avoided. In the particular arrangement illustrated in the figures, locking arrangement 20 includes a first holding member 22, a second holding member 24, and a third holding member 26. Each of first, second, and third holding members 22, 24, 26 are secured to base 12 at mounting surface 14.

First holding member 22 is constructed and arranged to hold a first fluid-holding device, for example, a syringe, relative to a second fluid-holding device, for example, a syringe, and a connector on mounting surface 14 of base 12. In one example as illustrated in the FIGS., first holding member 22 includes a first pair of stops 28 with stop surfaces cantilevered from, or extending proud from mounting surface 14 of base 12. Preferably, first stops 28 comprise a pair of members which are easily attached to base 12, and are sufficiently rigid to hold all of the mixing components in place. In the particular embodiment which is illustrated in FIG. 2, first stops 28 include a pair of pegs 30, 32 mounted into base 12. Pegs 30, 32 preferably are removably mounted, in order to accommodate different sized syringes. However, it is contemplated that they may be permanently secured as well. First stops 28 may also comprise pins, nails, tacks, or molded plastic elongated pieces or molded plastic contoured holders integral with, for example, a plastic base. Base 12 includes three pairs of apertures 35 for receiving pegs 30, 32. Pegs 30, 32 are spaced apart from each other to define a gap 34 (FIG. 1) therebetween. As will become apparent in further description, gap 34 is for accommodating a plunger of a syringe to be slidably held therethrough. The series of apertures 35 are for accommodating syringes of a variety of sizes (length and width). As illustrated in FIG. 1, gap 34 between each of the pairs of apertures 35 varies in size in order to allow for syringes of varying widths.

Second holding member 24 may be constructed similarly to first holding member 22. Second holding member 24 is constructed and arranged to hold a second fluid-holding device, for example, a syringe, relative to the first fluid-holding device and connector on mounting surface 14 of base 12. Second holding member is positioned on base 12 to hold the second fluid-holding device at an angle from the first fluid holding device. Second holding member 24 preferably includes a second pair of stops 36 cantilevered, or extending from base 12. In the particular arrangement illustrated in the figures, second stops 36 include first and second pegs 38, 40 with stop surfaces thereon. Apertures 41 in base accommodate removable pegs 38, and allow for syringes of varying sizes, as described above with respect to apertures 35. Pegs 38, 40 are spaced apart from each other to form a gap 42 (FIG. 1) therebetween. Gap 42 allows a plunger from a second syringe to slidably pass therethrough. As with first holding member 22, second holding member 24 may comprise other structure with sufficient rigidity to hold the syringes in place, for example, pins, nails, tacks, or molded plastic pins or pieces integral with the base.

Third holding member 26 is constructed and arranged to hold a connector for connecting the first fluid holding device and second fluid holding device relative to the fluid holding devices on the mounting surface 14 of the base 12. The third holding member 26 is positioned on base 12 in axial alignment with both first holding member 22 and second holding member 24. It is preferred that third holding member 26 be of a construction of sufficient rigidity to firmly hold a connector in place. One particular third holding member 26 includes a third pair of stops 44 and a fourth pair of stops 46, each cantilevered, or extending from base 12.

Specifically, in the exemplary embodiment illustrated in FIG. 2, third and fourth pairs of stops 44, 46 include pegs 48, 50, 52, 54. Pegs 48, 50, 52, 54 are mounted within base 12 in apertures 55 to support and resist force from the syringes along four different sides, which will be explained in more detail below. Pegs 48, 50, 52, 54 may be permanently mounted or removably mounted in base 12. Third and fourth stops 44, 46 may also include other structure with sufficient rigidity to hold and support the mixing devices, for example, pins, nails, tacks, or molded plastic pins or substrates integral with the base.

In accordance with the invention, the mixing arrangement includes a first syringe being held by the first holding member. As embodied herein, a first syringe 56 includes a barrel 58 for containing a first fluid to be mixed. For example, the fluid could be a peptide antigen. Barrel 58 includes a flange 60 at one end thereof. Slidably held within barrel 58 is a plunger 62 with a polymeric tip 64 at one end, and a pushing surface 66 at an opposite end. Plunger 62 pushes the fluid contained within barrel 58 through the barrel toward an outlet of syringe 56. Plunger 62 rests within gap 34 between first stops 28. Flange 60 of barrel 58 engages and abuts the first pair of stops 28 at pegs 30, 32.

A second syringe 68 may be constructed similarly to first syringe 56. Second syringe 68 includes a barrel 70 for holding another kind of fluid, for example, adjuvant. Barrel 70 includes flange 72, and slidably accommodates a plunger 74 having a polymeric tip 76 and a pushing surface 78 thereon. Plunger 74 is slidably held within gap 42 between peg 38 and peg 40. Flange 72 engages and abuts pegs 38, 40.

In accordance with the invention, the mixing arrangement includes a connector for connecting the first and second syringes. As embodied herein, an example of one preferred connector is illustrated in the figures as a three-way stopcock 80. Each of first and second syringes 56, 68 are mounted within stopcock 80 at entry ports 82, 84. Typically, the syringes are interference fitted into the stopcock 80. Stopcock 80 includes a main body 86 defining four exterior corners 88, 90, 92, 94. That is, stopcock 80 generally is cross-shaped, and exterior corners 88, 90, 92, 94 are located at the perimeter of the intersection of the cross. Stopcock 80 includes a flow control lever 96 for selectively opening and closing a valve within stopcock 80 for the selective flow of fluid between syringes 56 and 68. Because stopcock 80 is a 3-way stopcock, there is an additional port 98. In use of the present invention, port 98 is typically closed off by the internal valve, so that there is fluid communication only between ports 82, 84, and, thus, first and second syringes 56, 68. Third and fourth pairs of stops 44, 46 are positioned to engage and hold stopcock 80 in place on base 12. One manner this is accomplished is illustrated in FIG. 2 by positioning peg 48 in corner 90, peg 50 in corner 88, peg 52 in corner 92, and peg 54 in corner 94. The relative positioning of the third and fourth pairs of stops 44, 46 with respect to stopcock 80 and the syringes 56, 68 leads to an arrangement which allows for easy and convenient mixing of the fluids within the two syringes while avoiding the disengagement of stopcock 80 from either and both of the syringes. Third and fourth stops 44, 46 resist forces exerted thereon by the pressure of the fluids flowing through the syringes and into the stopcock. The first and second pairs of stops 28, 36 resist forces caused by back pressure of fluids flowing through the syringes and into stopcock 80. Therefore, it can be appreciated that the arrangement permits the mixing of fluids while preventing the disengagement of parts due to high pressure.

A method for mixing two fluids, such as adjuvant and antigens is as follows. A base is provided with first, second, and third holding members secured to the base. Depending on the size of the syringe used, the holding members may be adjusted on the base to accommodate the appropriate size syringe. For example, pegs may be moved closer or farther away from the third holding member, depending on the size desired. The third holding member may be positioned to be axially aligned with the first and second holding members. The first holding member and second holding member may be positioned such that when they are holding syringes, the syringes will be at about a 90° angle with respect to each other. One suitable base with holding members includes that as illustrated in FIGS. 1 and 2 at 12.

A first syringe 56 is filled with the first fluid to be mixed. For example, the first syringe may hold an adjuvant. Next, a second syringe 68 is filled with a second fluid for mixing, for example, antigens. Next, a connector such as a three-way stopcock 80 is connected to the two syringes.

The two syringes connected by the stopcock are mounted on the base 12. The first syringe is mounted on the base in a manner to engage the flange 60 of the syringe against an engagement surface of the first holding member. For example, if the first holding member includes a pair of pegs projecting from the base, the flange 60 is abutted against the main surface of the pegs 30, 32 with the plunger located in a gap between the pegs. The second syringe 68 is mounted on the base 12 such that the flange 72 on the syringe engages and abuts against the second holding member. For example, if the second holding member includes pegs projecting from the surface of the base, the flange 72 is positioned to abut against the main surface of the pegs 38, 40 with the plunger in a gap between the pegs. The three-way stopcock 80 is mounted to be held by the third holding member and positioned in place. For example, if the three-way stopcock has four exterior corners, the stopcock is positioned within the holding member such that a pin or peg engages each of the four exterior corners 88, 90, 92, 94.

After the syringes and stopcock are mounted, the two fluids may be mixed together. This may be accomplished by depressing one of the plungers in one of the syringes to push the fluid through the outlet of the syringe. This causes the other plunger to move outwardly from the barrel and draw up the fluid from the first syringe into the second syringe. Because the second syringe already contains some of the second fluid, the two fluids are mixed in the second syringe. The second syringe plunger may then be depressed, to push the mixture into the first syringe. This process is repeated, pumping the fluids back and forth between the two syringes until the fluids are adequately mixed. Ultimately, the final mixture is drawn into a single syringe, such as the second syringe. The second syringe containing the mixture, for example, an emulsification of adjuvant and antigen, may then be used on a laboratory animal. After use, both of the syringes and stopcock may be discarded. There is no cleanup required. This helps prevent contamination.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. An arrangement for mixing together two fluids, the arrangement comprising:

(a) a base including a supporting surface;

(b) a first holding member secured to said base; said first holding member constructed and arranged to hold a first syringe relative to a second syringe and a connector; said first holding member including a first pair of stops extending from said base;

(c) a second holding member secured to said base; said second holding member constructed and arranged to hold the second syringe relative to the first syringe and the connector;
(i) said second holding member being positioned on said base to hold the second syringe at a first angle from the first syringe; and (d) a third holding member secured to said base; said third holding member constructed and arranged to hold the connector relative to the first syringe and second syringe;
(i) said third holding member being positioned on said base in axial alignment with both said first holding member and said second holding member.

2. An arrangement according to claim 1, wherein:
(a) said second holding member includes a second pair of stops extending from said base.

3. An arrangement according to claim 2, wherein:
(a) said third holding member includes a third and a fourth pair of stops extending from said base.

4. An arrangement according to claim 3, wherein:
(a) said first angle is about 90 degrees.

5. An arrangement according to claim 4, wherein:
(a) said base includes a plexiglass board being substantially rectangular.

6. An arrangement according to claim 3, further including:
(a) a first syringe being held by said first holding member; said first syringe including a first barrel for containing a first fluid, and a first plunger slidably positioned within said first barrel;
(i) said first barrel including a first flanged surface engaging said first pair of stops; and
(b) a second syringe being held by said second holding member; said second syringe including a second barrel for containing a second fluid, and a second plunger slidably positioned within said second barrel;
(i) said second barrel including a second flanged surface engaging said second pair of stops.

7. An arrangement according to claim 6, further including:
(a) a connector adapted to connect said first and second syringes; said connector being held by and positioned between said third and fourth pairs of stops.

8. An arrangement according to claim 7, wherein:
(a) said connector includes a three-way stopcock.

9. An arrangement according to claim 7, wherein:
(a) said first pair of stops defines a first gap therebetween; and
(b) said first plunger is slidably positioned within said first gap.

10. An arrangement according to claim 9, wherein:
(a) said second pair of stops defines a second gap therebetween; and
(b) said second plunger is slidably positioned within said second gap.

11. An arrangement according to claim 3, wherein:
(a) each of said first, second, third, and fourth pairs of stops comprises removable pegs.

12. A mixing apparatus comprising:
(a) a base having a mounting surface;
(b) a first syringe positioned on said mounting surface;
(c) a second syringe positioned on said mounting surface;
(d) a connector connecting the first syringe and the second syringe; said connector being positioned on said mounting surface; and
(e) a locking arrangement secured to said base; said locking arrangement being constructed and arranged to prevent the connector from disengaging from both the first and second syringes;
(i) said locking arrangement including a first stop member engaging said first syringe; a second stop member engaging said second syringe; and a third stop member engaging said connector.

13. A mixing apparatus according to claim 12, wherein:
(a) said first stop member includes a first pair of pegs; said first syringe includes a first flange and a first plunger, wherein the first flange engages the first pair of pegs, and the plunger is slidably positioned between each of the first pair of pegs; and
(b) said second stop member includes a second pair of pegs; said second syringe includes a second flange and a second plunger, wherein the second flange engages the second pair of pegs, and the second plunger is slidably positioned between each of the second pair of pegs.

14. A mixing apparatus according to claim 13, wherein:
(a) said connector comprises a 3-way stopcock having at least four exterior corners; and
(b) said third stop member includes at least four pegs, each of said at least four pegs engaging said stopcock at a respective one of said exterior corners.

15. A mixing apparatus according to claim 12, wherein:
(a) said first and second stop members are adjustable to accommodate sizes of the first and second syringes.

16. A method for mixing comprising steps of:
(a) providing a base; a first holding member secured to the base; a second holding member secured to the base; and a third holding member secured to the base;
(b) connecting a first syringe holding a first fluid to a second syringe holding a second fluid using a 3-way stopcock; and
(c) positioning the first and second syringes connected by the stopcock on the base by engaging a first surface of the first syringe with the first holding member, engaging a second surface of the second syringe with the second holding member, and engaging the stopcock with the third holding member.

17. A method according to claim 16, further including:
(a) after said step of positioning, mixing the first and second fluids by pumping the first and second fluids back and forth between the first and second syringes.

18. A method according to claim 16, further including:
(a) prior to said step of positioning, selecting said first and second holding members based upon sizes of the first and second syringes.

* * * * *